(12) United States Patent
Liu et al.

(10) Patent No.: US 9,534,963 B2
(45) Date of Patent: Jan. 3, 2017

(54) MAGNETIC NANO TEMPERATURE MEASUREMENT METHOD USING TRIANGLE WAVE EXCITATION MAGNETIC FIELD

(71) Applicant: Huazhong University of Science and Technology, Wuhan (CN)

(72) Inventors: Wenzhong Liu, Wuhan (CN); Jing Zhong, Wuhan (CN); Ling Jiang, Wuhan (CN); Ming Yang, Wuhan (CN); Pu Zhang, Wuhan (CN); Ming Zhou, Wuhan (CN)

(73) Assignee: HUAZHONG UNIVERSITY OF SCIENCE AND TECHNOLOGY (CN)

( * ) Notice: Subject to any disclaimer, the term of this patent is extended or adjusted under 35 U.S.C. 154(b) by 151 days.

(21) Appl. No.: 14/412,443

(22) PCT Filed: Dec. 14, 2013

(86) PCT No.: PCT/CN2013/089445
§ 371 (c)(1),
(2) Date: Dec. 31, 2014

(87) PCT Pub. No.: WO2015/081585
PCT Pub. Date: Jun. 11, 2015

(65) Prior Publication Data
US 2016/0273971 A1    Sep. 22, 2016

(30) Foreign Application Priority Data
Dec. 4, 2013 (CN) .................... 2013 1 06460589

(51) Int. Cl.
*A61B 5/01* (2006.01)
*G01K 7/36* (2006.01)
*A61B 5/05* (2006.01)

(52) U.S. Cl.
CPC . *G01K 7/36* (2013.01); *A61B 5/01* (2013.01); *A61B 5/05* (2013.01); *A61B 2562/0285* (2013.01)

(58) Field of Classification Search
CPC .......... A61L 31/18; B82Y 25/00; B82Y 15/00; A61F 2/82
(Continued)

(56) References Cited

U.S. PATENT DOCUMENTS 8,498,837 B2    7/2013 Liu
9,301,693 B2 *  4/2016 Liu ......................... A61B 5/01
(Continued)

FOREIGN PATENT DOCUMENTS

CN    102156006    8/2011
CN    103156581    6/2013
(Continued)

OTHER PUBLICATIONS

PCT International Search Report for PCT/CN2013/089445 filed Dec. 14, 2013 in the name of Huazhong University of Science and Technology.
(Continued)

*Primary Examiner* — Edward Raymond
(74) *Attorney, Agent, or Firm* — Wenhua Yu

(57) ABSTRACT

Provided is a magnetic nano temperature measurement method under a triangle wave excitation magnetic field relating to a technical field of nano measurement. The method further comprises steps of: (1) positioning a magnetic nano sample at a measured object; (2) applying a triangle wave excitation magnetic field on area of the magnetic nano sample; (3) detecting a triangle wave excitation magnetic field-time curve and a magnetization-time curve of the magnetic nano sample; (4) obtaining a magnetizing curve of the magnetic nano sample, namely excitation magnetic field-magnetization curve, by the triangle wave excitation magnetic field curve and the magnetization curve, and sampling the magnetizing curve to obtain magnetization $M_i$ of the magnetic nano sample under excitation magnetic (Continued)

field $H_i$; and (5) determining temperature of the measured object by curve fitting with excitation magnetic field $H_i$ as input, magnetization $M_i$ as output, and a relationship between the excitation magnetic field and the magnetization as objective function. The invention obtains a magnetizing curve rapidly using a triangle wave excitation magnetic field, and realizes real-time and precise temperature measurement based on magnetic nanoparticles by inversion algorithms according to the magnetizing curve based on a temperature measurement model of magnetic nanoparticles under a DC magnetic field.

5 Claims, 4 Drawing Sheets

(58) Field of Classification Search
USPC .......................................... 702/130, 182–185
See application file for complete search history.

(56) References Cited

U.S. PATENT DOCUMENTS

| 2009/0068112 | A1 | 3/2009 | Haik |
| 2009/0068114 | A1 | 3/2009 | Haik |
| 2009/0074670 | A1 | 3/2009 | Haik |
| 2012/0184872 | A1 | 7/2012 | Haik |
| 2012/0239341 | A1 | 9/2012 | Liu |
| 2013/0129630 | A1 | 5/2013 | Haik |

FOREIGN PATENT DOCUMENTS

| EP | 2600128 | 6/2013 |
| JP | 2013517515 | 5/2013 |
| WO | 2012119329 | 9/2012 |

OTHER PUBLICATIONS

PCT Written Opinion for PCT/CN2013/089445 filed Dec. 14, 2013 in the name of Huazhong University of Science and Technology.
English translation of PCT Written Opinion for PCT/CN2013/089445 filed Dec. 14, 2013 in the name of Huazhong University of Science and Technology.
Zhong J. et al. "Real-time magnetic nanothermometry: The use of magnetization of magnetic nanoparticles assessed under low frequency triangle-wave magnetic fields." *Review of Scientific Instruments* 85, 094905 (2014); doi: 10.1063/1.4896121.
Zhong J. et al. "A new approach for highly accurate, remote temperature probing using magnetic nanoparticles." *Scientific Reports* 4 : 6338 (2014); DOI: 10.1038/srep06338.

* cited by examiner

MAGNETIC NANO TEMPERATURE MEASUREMENT METHOD USING TRIANGLE WAVE EXCITATION MAGNETIC FIELD

CROSS REFERENCE TO RELATED APPLICATIONS

The present application is the US national stage of International Application PCT/CN2013/089445 filed on Dec. 14, 2013 which, in turn, claims priority to Chinese Patent Application CN2013106460589 filed on Dec. 4, 2013.

FIELD OF THE INVENTION

The invention relates to a technical field of nano measurement, and more particularly to a temperature measurement method based on magnetization of magnetic nanoparticles using a triangle wave excitation magnetic field, which is especially applicable for temperature measurement in vivo.

BACKGROUND OF THE INVENTION

Temperature is one of physical quantities of the seven basic units set by the International System of Units and is also one of the most basic physical quantities of materials in the nature. Temperature measurement is of great importance for cognition of nature of materials in the nature. Magnetic nano temperature measurement method, a brand new temperature measurement method characterized in non-invasion, obtains temperature information mainly by measuring magnetization of magnetic nanoparticles and by inverse calculation based on certain model. Non-invasion property of magnetic nano temperature measurement method makes it have broad application prospects under special circumstances such as deeply in vivo and in other confined spaces.

Temperature measurement deeply in vivo and in other confined spaces remains a worldwide problem severely hindering development of related applications in the biomedical field such as tumor hyperthermia and drug transportation. Tumor hyperthermia technique, a tumor surgery known as the "Green Treatment" characterized in non-invasion or mini-invasion, treats a tumor mainly by differences of temperature tolerance between normal cells and tumor cells in vivo. Drug transportation technique releases a drug at a designated location and a predetermined amount by magnetic nanoparticles coated with drug laden polymer and by RF heating, where measuring and controlling temperature of the magnetic nanoparticles is critical to releasing the drug at a designated location and a predetermined amount. Unfortunately, at present, although temperature measurement technique under normal circumstances such as thermal resistances has already been very mature with properties of high precision and high real-time, temperature measurement technique under special circumstances such as deeply in vivo remains developing slowly. Challenges in temperature measurement in vivo mainly lie in the special circumstance in vivo and its safety requirements, which makes contact and non-contact temperature measurement methods in prior art inapplicable. Therefore, breakthrough in temperature measurement in vivo is bringing a technical revolution to related biomedical applications, and temperature measurement in vivo with high precision and high real-time remains a worldwide problem to be solved.

Development of related magnetic measurement technology brings twilight to solving the worldwide problem of precise and real-time temperature measurement in vivo. In recent years, development of magnetic resonance thermometry provides a reliable solution to temperature measurement in vivo. In 2008, Warren et al. realized high-precision temperature imaging by coherence of inner molecules in magnetic resonance, which is significant for research in tumor hyperthermia and drug transportation. Besides, in 2009, J. B. Weaver realized magnetic nano temperature measurement through experiments by amplitude ratio between the triple harmonic generation and the quintuple harmonic generation of AC magnetization of magnetic nanoparticles. In 2012, Liu Wenzhong realized precise temperature measurement using magnetic nanoparticles by DC magnetic susceptibility of magnetic nanoparticles and by derivation and experimental verification of theoretical models based on Langevin's function model, and finished theoretical model research on temperature measurement using magnetic nanoparticles by AC magnetic susceptibility of magnetic nanoparticles and by simulation afterwards. The researches pave the way for non-invasive temperature measurement in vivo, however, due to lack of proper theoretical model research and adequate experimental research, magnetic nano temperature measurement technique remains immature, in particular, real-time and precise temperature measurement technique lacks adequate theoretical and experimental researches. Therefore, realizing non-invasive, real-time and precise temperature measurement remains an urgent problem to be resolved in technical fields like biomedicine.

SUMMARY OF THE INVENTION

In view of the above-mentioned problems, it is an objective of the invention to provide a magnetic nano temperature measurement method under a triangle wave excitation magnetic field, so as to realize real-time and precise temperature measurement in vivo.

To achieve the above objective, there is provided a magnetic nano temperature measurement method under a triangle wave excitation magnetic field, comprising steps of:

(1) positioning a magnetic nano sample at a measured object;

(2) applying a triangle wave excitation magnetic field on area of the magnetic nano sample;

(3) detecting a triangle wave excitation magnetic field-time curve and a magnetization-time curve of the magnetic nano sample;

(4) obtaining a magnetizing curve of the magnetic nano sample, namely excitation magnetic field-magnetization curve, by the triangle wave excitation magnetic field-time curve and the magnetization-time curve, and sampling the excitation magnetic field-magnetization curve to obtain magnetization $M_i$ of the magnetic nano sample under excitation magnetic field $H_i$, where i=1, . . . , n and n is the total number of sampling points; and (5) determining temperature T of the measured object by curve fitting with excitation magnetic field $H_i$ as input, magnetization $M_i$ as output, and a relationship between the excitation magnetic field and the magnetization $$M_i = NM_s \left[ \coth\left(\frac{M_s H_i}{kT}\right) - \frac{kT}{M_s H_i} \right]$$

as objective function, where N is concentration of the magnetic nano sample, $M_s$ is effective magnetic moment of a magnetic nanoparticle, and k is Boltzmann's constant.

Furthermore, step (3) further performs two-fold averaging on each of the periodic curve segment of triangle wave excitation magnetic field and that of magnetization by the same method as follows:

Obtaining multiple continuous periodic curve segments from the curve;

obtaining a periodic curve segment per unit period by performing superimposed averaging on the continuous periodic curve segments;

sampling the periodic curve segment sequentially;

dividing the periodic curve segment into four curve segments ranging from a first zero value to a peak, from the peak to a second zero value, from the second zero value to a valley, and from the valley to a third zero value respectively;

arranging sampling points of the curve segment ranging from a first zero value to a peak sequentially to form a first set of sampling points;

arranging sampling points of the curve segment ranging from the peak to a second zero value sequentially to form a second set of sampling points;

averaging each point of the first set of sampling points and a sequentially corresponding point of the second set of sampling points to obtain a first array of intermediate mean values;

arranging sampling points of the curve segment ranging from the second zero value to a valley sequentially to form a third set of sampling points;

arranging sampling points of the curve segment ranging from the valley to a third zero value sequentially to form a fourth set of sampling points;

averaging each point of the third set of sampling points and a sequentially corresponding point of the fourth set of sampling points to obtain a second array of intermediate mean values; and averaging each value of the first array of intermediate mean values and the absolute value of a sequentially corresponding value of the second array of intermediate mean values to obtain a sampling array illustrating a variation trend between a zero value and a peak in a period.

Furthermore, a smoothing process is performed on the periodic curve segment which is further illustrated as follows: updating Y-axis value of a first point of the periodic curve segment to an average of that of a $1^{st}$ point to a Nth point, updating Y-axis value of a second point to an average of that of a (N+1)th point to a (2N)th point, updating Y-axis value of a third point to an average of that of a (2N+1)th point to a (3N)th point, . . . , and so on until finishing updating Y-axis values for the whole periodic curve segment.

Furthermore, step (5) further comprises steps of:

substituting a sampling array of excitation magnetic field $(H_1, H_2, \ldots, H_n)$ and a sampling array of magnetization $(M_1, M_2, \ldots, M_n)$ into the Langevin's function $$M_i = a\left[\coth(bH_i) - \frac{1}{bH_i}\right]$$

as input, where $a=NM_s$ and $$b = \frac{M_s}{kT},$$

and obtaining optimum values a* and b* of variables a and b with a target of minimum error $\alpha=\|S\|^2$, where $$S = [\delta_1, \delta_2, \cdots \delta_n]^T, \delta_i = a\left[\coth(bH_i) - \frac{1}{bH_i}\right] - M_i,$$

i=1, . . . , n, n is the total number of sampling points, coth( ) represents the hyperbolic cotangent function, and the superscript T represents transposition; and calculating temperature $$T = \frac{M_s}{b*k}$$

according to optimum value b* of variable b.

Furthermore, the frequency of the triangle wave excitation magnetic field ranges from 0.5 Hz to 100 Hz, and the amplitude of the triangle wave excitation magnetic field ranges from 10 Gs to 1000 Gs.

Advantages of the present invention comprise:

applying a low-frequency triangle wave excitation magnetic field on area of a magnetic nano sample, detecting the excitation magnetic field and magnetization of the magnetic nano sample simultaneously, and calculating by Langevin's function model and related inversion algorithms (Levenberg-Marquardt) for the reason that phase difference between magnetization of the magnetic nano sample and the excitation magnetic field is negligible under the low-frequency triangle wave excitation magnetic field, and the magnetizing curve (excitation magnetic field-magnetization curve) can be described by the Langevin's function, so as to obtain precise temperature information in real time; and furthermore, considering that hysteresis occurs in the magnetizing curve of the magnetic nano sample, namely two magnetizing curves obtained by magnetization of the magnetic nano sample increasing and decreasing with the excitation magnetic field respectively are not identical, averaging multiple periods of a excitation magnetic field curve and a magnetization curve of the magnetic nano sample detected in certain time period respectively, and performing two-fold averaging on a periodic curve segment, so as to obtain a magnetizing curve of the magnetic nano sample without hysteresis and further improve measurement accuracy.

Overall, the present invention detects a magnetizing curve of a magnetic nano sample rapidly using a triangle wave excitation magnetic field, calculates temperature information by related inverse algorithms and Langevin's function model, and realizes rapid and precise temperature measurement. Tests show that accuracy of magnetic nano temperature measurement reaches 0.1K according to the method of the present invention.

BRIEF DESCRIPTION OF THE ACCOMPANYING DRAWINGS

SPECIFIC EMBODIMENTS OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Firstly, the principle of magnetic nano temperature measurement is described briefly in order to better illustrate the present invention. Magnetic nanoparticle is a superparamagnetic material and its magnetizing curve follows the Langevin's paramagnetic theorem:

$$M = NM_S\left[\coth\left(\frac{M_S H}{kT}\right) - \frac{kT}{M_S H}\right] = a\left[\coth(bH) - \frac{1}{bH}\right]$$

Where $a = NM_s$, $$b = \frac{M_s}{kT},$$

Figure 1:
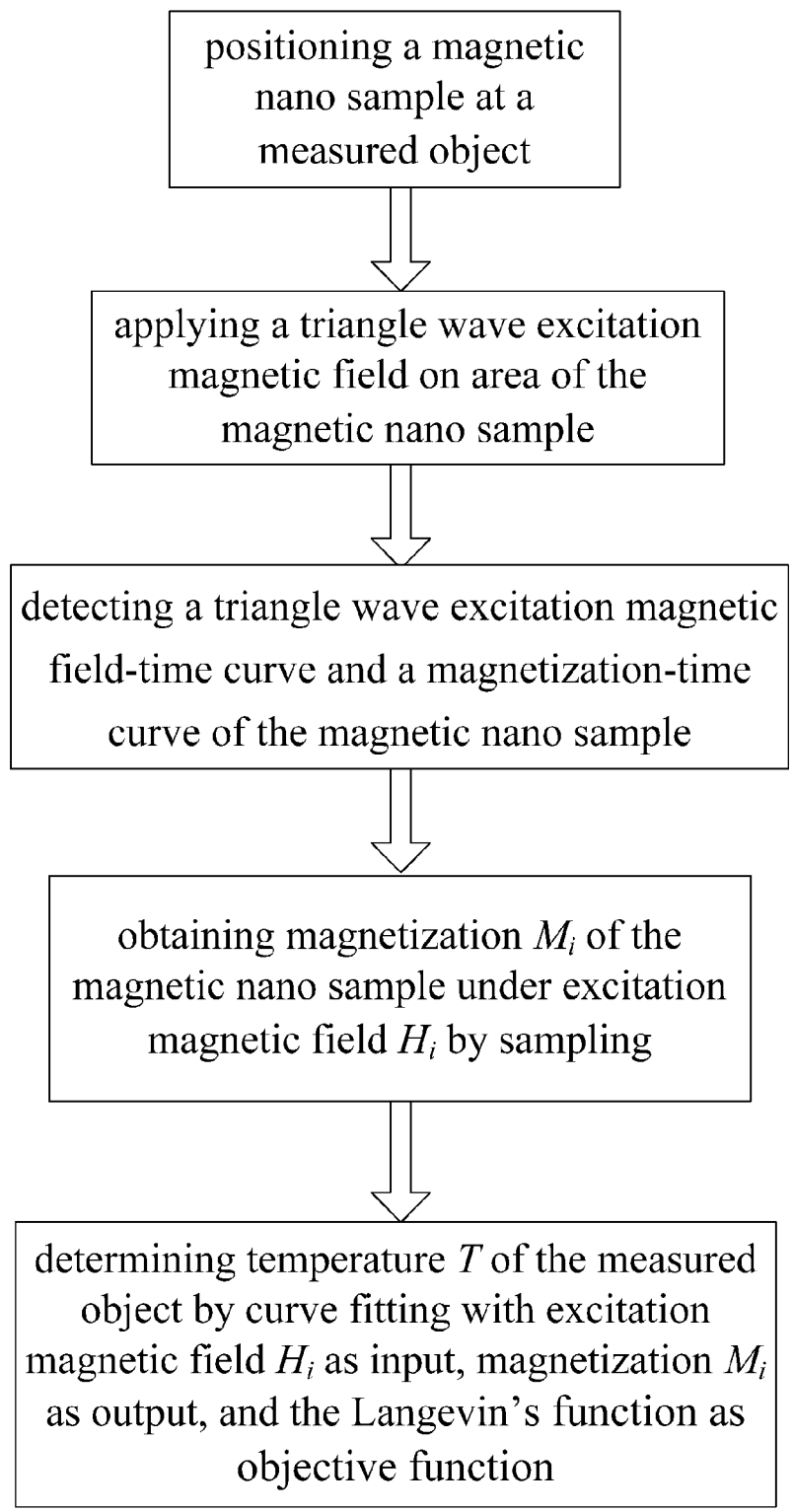
FIG. 1 is a flow chart of a temperature measurement method according to the present invention.
Figure 1:
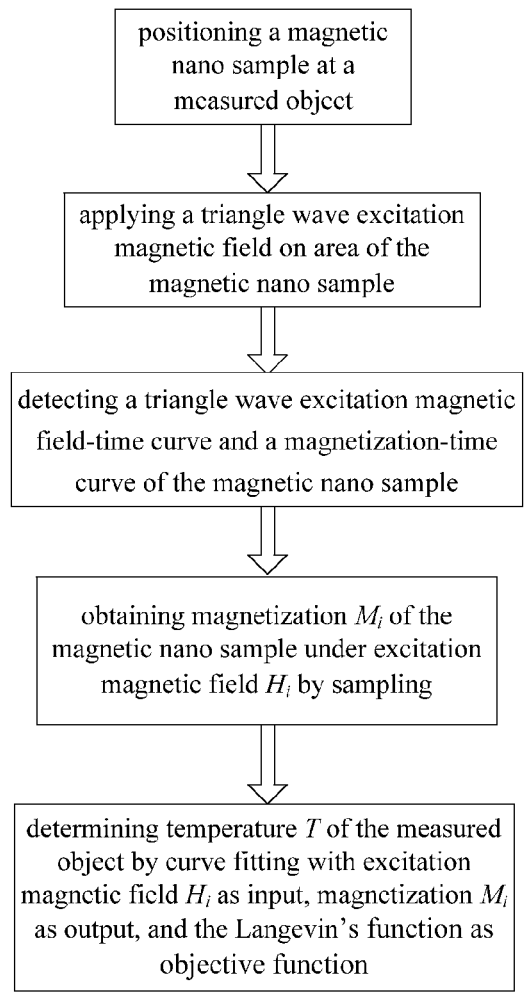
Figure 2:
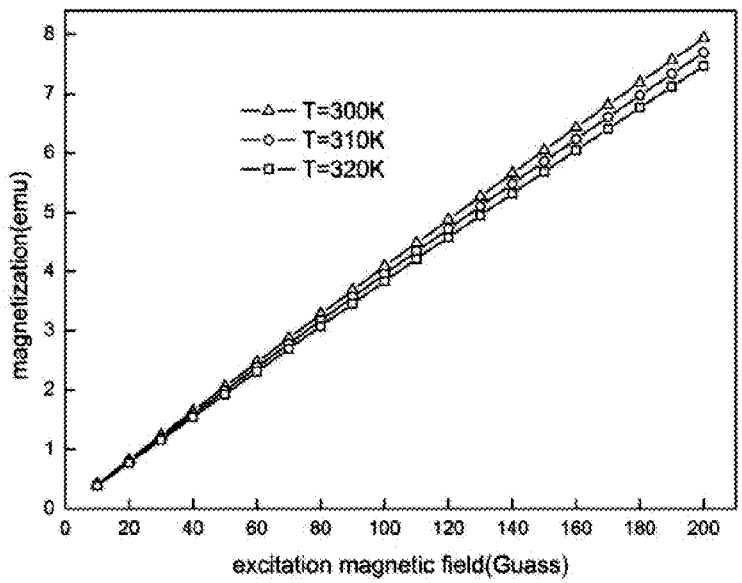
FIG. 2 shows magnetizing curves of magnetic nanoparticles at different temperatures.

M is magnetization of a magnetic nano sample, N is concentration of the magnetic nano sample, $M_s$ is effective magnetic moment of a magnetic nanoparticle, H is a triangle wave excitation magnetic field, k is Boltzmann's constant, and T is absolute temperature. It can be concluded from the Langevin's function that the magnetizing curve of magnetic nanoparticles is temperature sensitive which changes with the temperature (as in FIG. 2). Therefore, magnetic nano temperature measurement can be realized by measuring the magnetizing curve of magnetic nanoparticles and by using the theoretical model of the Langevin's function and related inversion algorithms.

The magnetizing curve (excitation magnetic field-magnetization curve) of magnetic nanoparticles should be obtained rapidly so as to measure the temperature of magnetic nanoparticles in real time. At high frequencies, phase difference between a excitation magnetic field and magnetization of magnetic nanoparticles exists and is affected by parameters such as temperature and the particle size, which makes the magnetizing model of magnetic nanoparticles quite complicated and accurately measuring the magnetizing curve of magnetic nanoparticles difficult. The present invention found that under a low-frequency triangle wave excitation magnetic field, phase difference between magnetization of magnetic nanoparticles and the excitation magnetic field is negligible and the magnetizing process of magnetic nanoparticles can be described by the Langevin's function. Therefore, a magnetizing curve of magnetic nanoparticles can be obtained accurately in real time by detecting a magnetization curve of magnetic nanoparticles under a low-frequency triangle wave excitation magnetic field, so as to realize precise and real-time temperature measurement of magnetic nanoparticles.

Based on the above technical ideas, the present invention provides a magnetic nano temperature measurement method under a triangle wave excitation magnetic field, comprising steps of:

(1) positioning a magnetic nano sample at a measured object;

modifying surface of a magnetic nano sample to make it biocompatible and can be targeted to a measured vivo object by blood circulation;

(2) applying a triangle wave excitation magnetic field on area of the magnetic nano sample;

applying a triangle wave excitation magnetic field on area of the magnetic nano sample by Helmholtz coils, where there are certain requirements for both frequency and amplitude of the triangle wave excitation magnetic field where the frequency ranges from 0.5 Hz to 100 Hz for the reason that averaging by period is required to reduce noise and enough data points is required for each period, and the amplitude ranges from 10 Gs to 1000 Gs for the reason that amplitude of the triangle wave excitation magnetic field affects preset values of the excitation magnetic field and the total number n of data points for fitting;

(3) detecting the triangle wave excitation magnetic field and magnetization of the magnetic nano sample simultaneously;

detecting the excitation magnetic field and magnetization of the magnetic nano sample simultaneously by related sensors, processing the detected results by a signal conditioning circuit, collecting the excitation magnetic field and magnetization into a computer by a data acquisition card, and obtaining a excitation magnetic field curve and a magnetization curve of the magnetic nano sample;

(4) sampling magnetization $M_i$ of the magnetic nano sample under excitation magnetic field $H_i$;

sampling the triangle wave excitation magnetic field-time curve and the magnetization-time curve to obtain magnetization $M_i$ of the magnetic nano sample under excitation magnetic field $H_i$, where $i=1, \ldots, n$ and n is the total number of sampling points;

(5) establishing a theoretical model between the excitation magnetic field and magnetization of the sample according to the Langevin's paramagnetic theorem, and calculating the temperature in real time by related inverse algorithms;

determining temperature T of the measured object by curve fitting with excitation magnetic field $H_i$ as input, magnetization $M_i$ as output, and a relationship between the excitation magnetic field and the magnetization $$M_i = NM_s\left[\coth\left(\frac{M_s H_i}{kT}\right) - \frac{kT}{M_s H_i}\right]$$

as objective function, where $M_s$ is effective magnetic moment of a magnetic nanoparticle, and k is Boltzmann's constant.

Further description is as follows:

substituting excitation magnetic field ($H_1, H_2, \ldots, H_n$) and corresponding magnetization of the sample ($M_1, M_2, \ldots, M_n$) into the Langevin's function $$M = a\left[\coth(bH) - \frac{1}{bH}\right]$$

as input, where $a = NM_s$, $$b = \frac{M_s}{kT}$$

and b is a variable to be solved in an inverse algorithm, obtaining errors between theoretical values and experimental values of magnetization of the magnetic nano sample:

$$\begin{cases} \delta_1 = a\left[\coth(bH_1) - \frac{1}{bH_1}\right] - M_1 \\ \delta_2 = a\left[\coth(bH_2) - \frac{1}{bH_2}\right] - M_2 \\ \vdots \\ \delta_n = a\left[\coth(bH_n) - \frac{1}{bH_n}\right] - M_n \end{cases}$$

setting $S=[\delta_1, \delta_2, \ldots \delta_n]^T$ and $\alpha=S^TS=\|S\|^2$, where variables a and b reach optimal values and $F=S'S^T=0$ when the sum of squared errors $\alpha$ is minimum, predetermining initial parameters $(a_0,b_0)$ and termination conditions (error range, maximum number of iterations, etc.) which is determined by experiences and can be adjusted by test results, obtaining optimum parameters a* and b* by solving non-linear equations, and calculating temperature T by $$T = \frac{M_s}{b^*k}.$$

Advantageously, in step (4), an optimizing process is performed on the triangle wave excitation magnetic field-time curve and the magnetization-time curve, where Y-axis values of the triangle wave excitation magnetic field curve are discrete values of the excitation magnetic field and Y-axis values of the magnetization curve are discrete values of magnetization. The process is as follows:

(41) capturing a curve segment containing multiple consecutive periods from each of the triangle wave excitation magnetic field-time curve and the magnetization-time curve;

(42) obtaining a periodic curve segment of triangle wave excitation magnetic field per unit period by performing superimposed averaging on multiple continuous periodic curve segments of the triangle wave excitation magnetic field-time curve, and obtaining a periodic curve segment of magnetization per unit period by performing superimposed averaging on multiple continuous periodic curve segments of the magnetization-time curve; and

(43) performing two-fold averaging on each of the periodic curve segment of triangle wave excitation magnetic field and that of magnetization by the same method as follows and obtaining an array of triangle wave excitation magnetic field $H_i$ and an array of magnetization $M_i$:

dividing the periodic curve segment into four curve segments ranging from a first zero value to a peak, from the peak to a second zero value, from the second zero value to a valley, and from the valley to a third zero value respectively;

arranging sampling points of the curve segment ranging from a first zero value to a peak sequentially to form a first set of sampling points;

arranging sampling points of the curve segment ranging from the peak to a second zero value sequentially to form a second set of sampling points;

averaging Y-axis value of each point of the first set of sampling points and that of a sequentially corresponding point of the second set of sampling points to obtain a first array of intermediate mean values;

arranging sampling points of the curve segment ranging from the second zero value to a valley sequentially to form a third set of sampling points;

arranging sampling points of the curve segment ranging from the valley to a third zero value sequentially to form a fourth set of sampling points;

averaging Y-axis value of each point of the third set of sampling points and that of a sequentially corresponding point of the fourth set of sampling points to obtain a second array of intermediate mean values; and averaging each value of the first array of intermediate mean values and the absolute value of a sequentially corresponding value of the second array of intermediate mean values to obtain the array of triangle wave excitation magnetic field $H_i$ or the array of magnetization $M_i$ effectively illustrating a variation trend between a zero value and a peak in a period.

Figure 3:
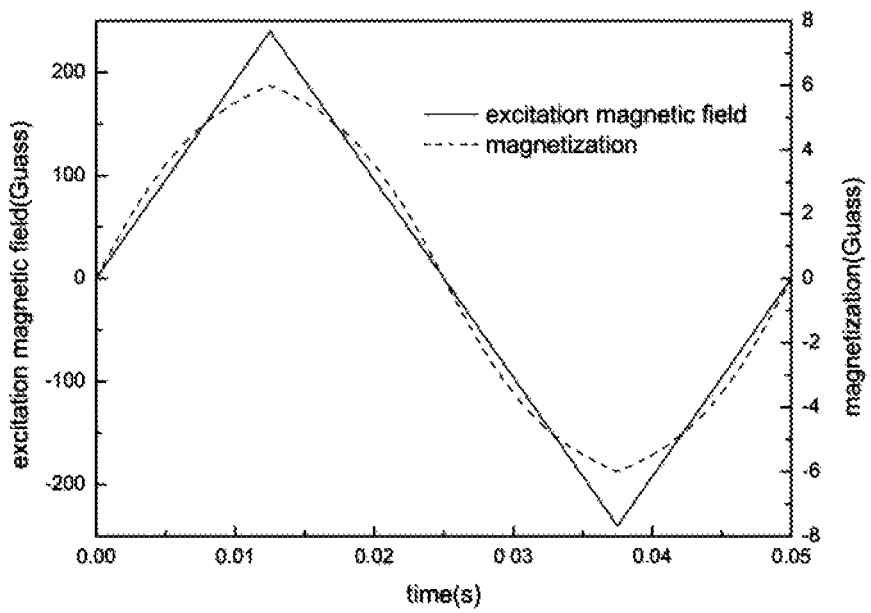
FIG. 3 shows an excitation magnetic field curve and a magnetization curve of magnetic nanoparticles respectively after averaging m periods by period.
Figure 4:
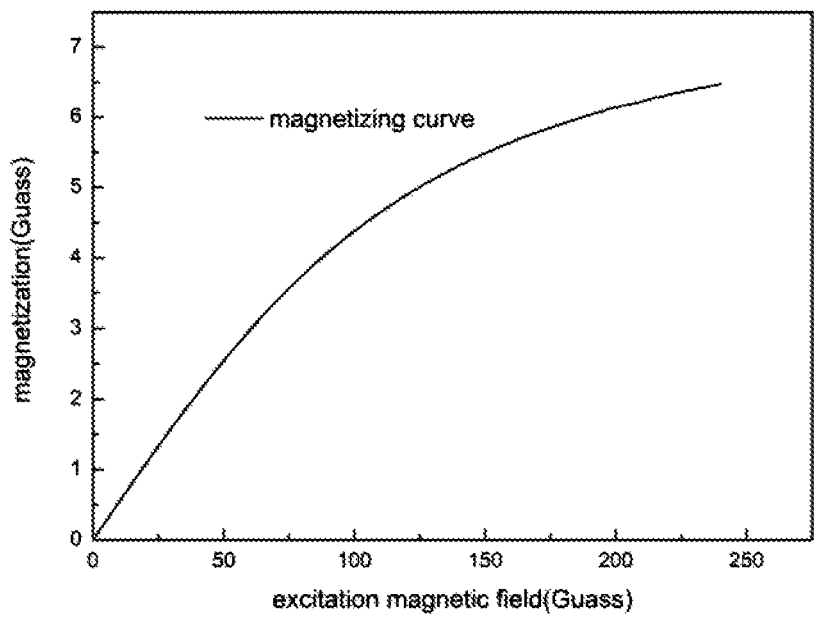
FIG. 4 shows a magnetizing curve of magnetic nanoparticles.

The process is realized specifically as follows:

presetting certain number of points required for the excitation magnetic field $(h_1, h_2, \ldots h_n)$ to obtain corresponding magnetization, where $h_1 \sim h_n$ is arranged in an ascending order;

resampling each of the curve segments ranging from a first zero value to a peak (excitation magnetic field and magnetization) in FIG. 3 to obtain magnetization $(M1_{n+1}, M1_{n+2}, \ldots M1_{n+n})$ corresponding to excitation magnetic field $(H1_{n+1}, H1_{n+2}, \ldots H1_{n+n})$ whereby deriving a set of points $(H1_{n+1}, M1_{n+1}), (H1_{n+2}, M1_{n+2}), \ldots, (H1_{n+n}, M1_{n+n})$, where $H1_{n+i}$ corresponds to a point of the curve segment with a minimum absolute value of $H1_{n+i}-h_i$, and $i=1, \ldots, n$;

resampling each of the curve segments ranging from the peak to a second zero value (excitation magnetic field and magnetization) in FIG. 3 to obtain magnetization $(M2_1, M2_2, \ldots M2_n)$ corresponding to excitation magnetic field $(H2_1, H2_2, \ldots H2_n)$ whereby deriving a set of points $(H2_1, M2_1), (H2_2, M2_2), \ldots, (H2_n, M2_n)$, where $H2_i$ corresponds to a point of the curve segment with a minimum absolute value of $H2_i-h_{n-i+1}$, and $i=1, \ldots, n$;

resampling each of the curve segments ranging from the second zero value to a valley (excitation magnetic field and magnetization) in FIG. 3 to obtain magnetization $(M2_{n+1}, M2_{n+2}, \ldots, M2_{n+n})$ corresponding to excitation magnetic field $(H2_{n+1}, H2_{n+2}, \ldots, H2_{n+n})$ whereby deriving a set of points $(H2_{n+1}, M2_{n+1}), (H2_{n+2}, M2_{n+2}), \ldots, (H2_{n+n}, M2_{n+n})$, where $H2_{n+i}$ corresponds to a point of the curve segment with a minimum absolute value of $H2_{n+i}-(-h_i)$, and $i=1, \ldots, n$;

resampling each of the curve segments ranging from the valley to a third zero value (excitation magnetic field and magnetization) in FIG. 3 to obtain magnetization $(M1_1, M1_2, \ldots, M1_n)$ corresponding to excitation magnetic field $(H1_1, H1_2, \ldots, H1_n)$ whereby deriving a set of points $(H1_1, M1_1), (H1_2, M1_2), \ldots, (H1_n, M1_n)$, where $H1_i$ corresponds to a point of the curve segment with a minimum absolute value of $H1_i-(-h_{n-i+1})$, and $i=1, \ldots, n$; and obtaining two sets of points $(H1_1, M1_1), (H1_2, M1_2), \ldots, (H1_{2n}, M1_{2n})$ and $(H2_1, M2_1), (H2_2, M2_2), \ldots, (H2_{2n}, M2_{2n})$ by the above processes, setting $H3_j=(H1_j+H2_{2n-j+1})/2$ and $M3_j=(M1_j+M2_{2n-j+1})/2$ whereby deriving a set of data points $(H3_j, M3_j)$, where $j=1, 2, \ldots, 2n$, and setting $H_i=(H3_{n+i}-H3_{n-i+1})/2$ and $M_i=(M3_{n+i}-M3_{n-i+1})/2$ whereby deriving a set of data points $(H_i, M_i)$ shown in FIG. 4, where $i=1, \ldots, n$, which is helpful for eliminating the effect of possible hysteresis on the accurate of temperature measurement.

Besides, after obtaining a periodic curve segment of excitation magnetic field by averaging any curve segment of triangle wave excitation magnetic field containing m consecutive periods by period and a periodic curve segment of magnetization of magnetic nanoparticles by averaging any curve segment of magnetization of the sample containing m consecutive periods by period, an averaging process by N points (ex. eight points) may be performed on each of the periodic curve segment of excitation magnetic field and that of magnetization (shown in FIG. 3). The averaging method is as follows: obtaining a first point of an averaged curve by averaging a $1^{st}$ point to an $8^{th}$ point of the original curve (excitation magnetic field and magnetization), obtaining a second point of the averaged curve by averaging a $9^{th}$ point to a $16^{th}$ point of the original curve, . . . , and so on. The above two averaging algorithms help to improve the accuracy of magnetization measurement of magnetic nanoparticles, so as to improve the accuracy of magnetic nano temperature measurement.

In practice, real-time measurement is realized by dividing the measuring time period into several time periods in advance and processing multiple periods of the triangle wave excitation magnetic field and multiple periods of magnetization of the sample in each time period by the above method.

A curve between the excitation magnetic field and magnetization is derived finally (shown in FIG. 4), and magnetization $M_i$ of magnetic nanoparticles under excitation magnetic field $H_i$ after the averaging processes is further obtained whereby obtaining data points $(H_i, M_i)$ required for calculating temperature information by inversion. In practice, $Fe_3O_4$ magnetic nanoparticles are ferromagnetic which leads to hysteresis of the magnetizing curve of magnetic nanoparticles, namely two magnetizing curves obtained by magnetization of magnetic nanoparticles increasing and decreasing with an excitation magnetic field respectively are not identical. However, the above process can avoid hysteresis's impact on magnetic nano temperature measurement and improve the accuracy of temperature measurement. At certain frequency, period number m directly affects real-time of temperature measurement, therefore, m may be determined by requirements for real-time of temperature measurement.

Figure 5:
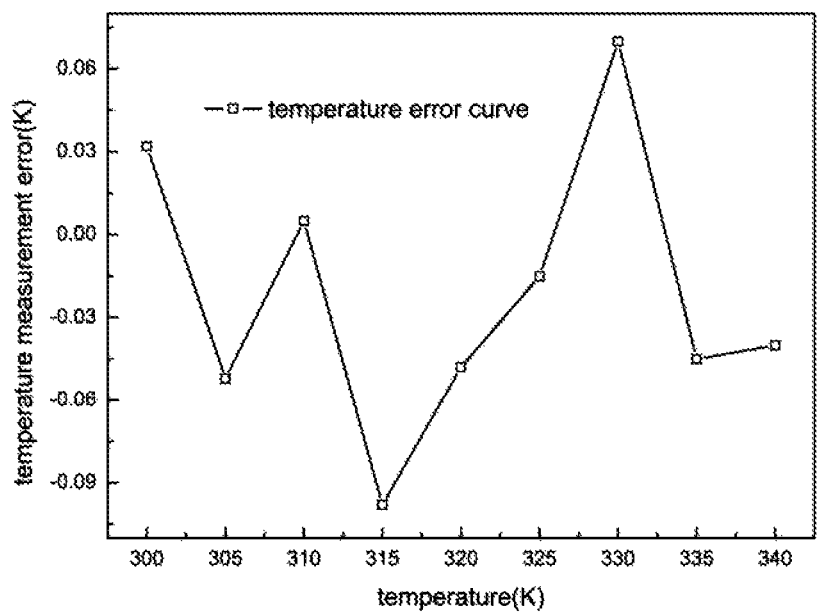
FIG. 5 is a schematic diagram of temperature measurement errors.

Simulation Example:

In order to study the effectiveness of the temperature measuring method, simulation data containing noise is used for testing the algorithm in simulation. Assume effective magnetic moment of a magnetic nanoparticle $M_s=5.2\times10^{-19}$ (should be tested repeatedly in experiment and is determined by parameters of a magnetic nano sample), frequency of the triangle wave excitation magnetic field $f=20$ Hz, and amplitude thereof Ha=245 Gauss. The number n of data points in each curve segment used for solving the nonlinear equations and step of the excitation magnetic field $\Delta H$ are determined by Ha. Gaussian white noise with a standard deviation of 0.01 is added to the excitation magnetic field and magnetization of the sample respectively. In simulation, temperature points are selected in every 5° C. in a range of 300~340° C., and the simulation result is illustrated in FIG. 5 showing that the accuracy of magnetic nano temperature measurement is better than 0.1K with a standard deviation of 0.05K. The experiment proves that the accuracy of the temperature measuring method is of great importance for research in temperature measurement in vivo.

While preferred embodiments of the invention have been described above, the invention is not limited to disclosure in the embodiments and the accompanying drawings. Any changes or modifications without departing from the spirit of the invention fall within the scope of the invention.

What is claimed is:

1. A magnetic nano temperature measurement method under a triangle wave excitation magnetic field, comprising steps of:
   (1) positioning a magnetic nano sample at a measured object;
   (2) applying said triangle wave excitation magnetic field on area of said magnetic nano sample;
   (3) detecting a triangle wave excitation magnetic field-time curve and a magnetization-time curve of said magnetic nano sample;
   (4) sampling said triangle wave excitation magnetic field-time curve and said magnetization-time curve thereby obtaining magnetization $M_i$ of said magnetic nano sample under excitation magnetic field $H_i$, where i=1, . . . , n and n is the total number of sampling points; and
   (5) determining temperature T of said measured object by curve fitting with excitation magnetic field $H_i$ as input, magnetization $M_i$ as output, and a relationship between the excitation magnetic field and the magnetization $$M_i = NM_s\left[\coth\left(\frac{M_sH_i}{kT}\right) - \frac{kT}{M_sH_i}\right]$$

as objective function, where N is concentration of said magnetic nano sample, $M_s$ is effective magnetic moment of a magnetic nanoparticle, and k is Boltzmann's constant.

2. The method of claim 1, wherein said step (4) comprises steps of:
   (41) capturing a curve segment containing multiple consecutive periods from each of said triangle wave excitation magnetic field-time curve and said magnetization-time curve;
   (42) obtaining a first periodic curve segment of said triangle wave excitation magnetic field per unit period by performing superimposed averaging on multiple continuous periodic curve segments of said triangle wave excitation magnetic field-time curve, and obtaining a second periodic curve segment of said magnetization per unit period by performing superimposed averaging on multiple continuous periodic curve segments of said magnetization-time curve; and
   (43) performing two-fold averaging on each of the first and second periodic curve segments thereby obtaining an array of triangle wave excitation magnetic field $H_i$ and an array of magnetization $M_i$; wherein said two-fold averaging on said first or second periodic curve segment is performed by:
   dividing the first or second periodic curve segment into a first curve segment ranging from a first zero value to a peak, a second curve segment ranging from the peak to a second zero value, a third curve segment ranging from the second zero value to a valley, and a fourth curve segment ranging from the valley to a third zero value;
   arranging sampling points of the first curve segment sequentially to form a first set of sampling points;
   arranging sampling points of the second curve segment sequentially to form a second set of sampling points;
   averaging Y-axis value of each point of the first set of sampling points and Y-axis value of a sequentially corresponding point of the second set of sampling points to obtain a first array of intermediate mean values;

arranging sampling points of the third curve segment sequentially to form a third set of sampling points;

arranging sampling points of the fourth curve segment sequentially to form a fourth set of sampling points;

averaging Y-axis value of each point of the third set of sampling points and Y-axis value of a sequentially corresponding point of the fourth set of sampling points to obtain a second array of intermediate mean values; and averaging each value of the first array of intermediate mean values and the absolute value of a sequentially corresponding value of the second array of intermediate mean values to obtain the array of triangle wave excitation magnetic field $H_i$ or the array of magnetization $M_i$ effectively illustrating a variation trend between a zero value and a peak in a period.

3. The method of claim 2, wherein in said step (42), a smoothing process is performed on each of the first and second periodic curve segments; wherein said smoothing process on the first or second periodic curve segment is performed by: updating Y-axis value of a first point of the first or second periodic curve segment to an average of that of a $1^{st}$ point to a $N^{th}$ point, updating Y-axis value of a second point to an average of that of a $(N+1)^{th}$ point to a $(2N)^{th}$ point, updating Y-axis value of a third point to an average of that of a $(2N+1)^{th}$ point to a $(3N)^{th}$ point, . . . , and so on until finishing updating Y-axis values for the whole of said first or second periodic curve segment.

4. The method of claim 1, wherein said step (5) further comprises steps of:

substituting a sampling array of excitation magnetic field $(H_1, H_2, \ldots, H_n)$ and a sampling array of magnetization $(M_1, M_2, \ldots, M_n)$ into the Langevin's function $$M_i = a\left[\coth(bH_i) - \frac{1}{bH_i}\right]$$

as input, where $a = NM_s$ and $$b = \frac{M_s}{kT},$$

and obtaining optimum values a* and b* of variables a and b with a target of minimum error $\alpha = \|S\|^2$, where $$S = [\delta_1, \delta_2, \cdots \delta_n]^T, \delta_i = a\left[\coth(bH_i) - \frac{1}{bH_i}\right] - M_i, i = 1, \ldots, n,$$

n is the total number of sampling points, coth( ) represents hyperbolic cotangent function, and superscript T represents transposition; and calculating temperature $$T = \frac{M_s}{b^* k}$$

according to said optimum value b* of said variable b.

5. The method of claim 1, wherein a frequency of said triangle wave excitation magnetic field ranges from 0.5 Hz to 100 Hz, and an amplitude of said triangle wave excitation magnetic field ranges from 10 Gs to 1000 Gs.

* * * * *